United States Patent [19]
Cannon et al.

[11] Patent Number: 5,690,490
[45] Date of Patent: Nov. 25, 1997

[54] METHOD AND APPARATUS FOR FABRICATION OF DENTAL RESTORATION BY PINHEAD MOLDING

[76] Inventors: Mark L. Cannon, 548 Wayland Ave., Kenilworth, Ill. 60043; George H. Boyd, 1351 W. Touhy, Apt. 1N, Chicago, Ill. 60626

[21] Appl. No.: 756,276

[22] Filed: Nov. 25, 1996

[51] Int. Cl.⁶ .................................................. A61C 5/04
[52] U.S. Cl. .................... 433/226; 433/214; 433/215; 433/223; 249/155; 425/2
[58] Field of Search ........................... 433/213, 214, 433/215, 223, 226; 249/155; 425/2

[56] References Cited

U.S. PATENT DOCUMENTS

| | | | |
|---|---|---|---|
| 3,861,044 | 1/1975 | Swinson, Jr. | 433/226 |
| 4,742,464 | 5/1988 | Duret et al. | 433/214 |
| 4,837,732 | 6/1989 | Brandestini et al. | 433/223 |
| 5,092,022 | 3/1992 | Duret | 433/213 |
| 5,192,560 | 3/1993 | Umetsu et al. | 249/155 |
| 5,224,049 | 6/1993 | Mushabac | 433/223 |
| 5,370,692 | 12/1994 | Fink et al. | 623/16 |
| 5,382,164 | 1/1995 | Stern | 433/223 |

FOREIGN PATENT DOCUMENTS 9014803  12/1990  WIPO ................................. 433/214

*Primary Examiner*—John J. Wilson
*Attorney, Agent, or Firm*—Laff, Whitesel, Conte & Saret, Ltd.

[57] ABSTRACT

A method for fabrication of a restoration for a patient's dentition by pinhead molding comprising the steps of examining the patient's dentition, restoring gross areas of tooth loss, and restoring proper anatomy and contour of the dentition, forming a first optically correct impression of the dentition and scanning the first impression to provide a first data set, appropriately isolating and preparing the patient's dentition for the dental restoration, forming a second optically correct impression of the dentition and scanning the second impression to form a second data set, comparing the first and second data sets and deriving a third data set based upon the comparison, the third data set being descriptive of a restoration to be prepared, and forming the restoration by pinhead molding of a flowable composite material in accordance with the third data set. An apparatus is also described for fabrication of a restoration for a patient's dentition.

18 Claims, 7 Drawing Sheets

METHOD AND APPARATUS FOR FABRICATION OF DENTAL RESTORATION BY PINHEAD MOLDING

FIELD OF THE INVENTION

This invention relates generally to dental prostheses or restorations, and in particular to a method and apparatus for producing a computer-assisted molded dental prosthesis or restoration with a natural anatomic form and the necessary occlusion for superior function.

BACKGROUND OF THE INVENTION

Before the introduction of computer-assisted machine tools for dentistry, the production of a dental restoration/prosthesis involved a number of complex, expensive, and/or time-consuming steps. First of all, dental anesthesia was often required for dental restorations. Shade had to be correctly determined and a study model fabricated, followed by dental preparation, occlusal registration, and temporization of dental preparations. A die was fabricated from an impression, and a laboratory constructed the dental prosthesis manually. Try-in and fitting of the laboratory work was accomplished, after removal of any temporaries. Then there was adjustment of occlusion, followed by cementation and polishing.

The above procedures were time consuming, required multiple appointments, temporization of the prepared dentition, and were costly due to laboratory fees. Because of the above-mentioned difficulties, methods have been introduced using computer-assisted machine tools to fabricate dental restorations and prostheses. Computer-assisted machine tools produce the dental prosthesis/restoration without relying on an outside laboratory, thereby reducing the number of visits, the cost of lab work, and the need for temporization.

The production of a dental restoration/prosthesis utilizing currently available computer-assisted machine tools for dentistry involves the following procedures:

dental anesthesia for dental restorations shade determination isolation of the dentition for preparation with a rubber dam preparation of the dentition application of an optically correcting spray/powder scanning of the dentition with a hand-held scanning device computer design of the restoration from the recorded image fabrication of the restoration/prosthesis in a milling device try-in and fitting of computer-milled work adjustment of occlusion grinding in of appropriate anatomy cementation and polishing Current methods involve the placement of a rubber dam (isolation procedure) and coating of the prepared teeth with an optically correct powder/spray. Positioning and anchoring the rubber dam is time-consuming, as is treatment of the dentition for optical compatibility with a hand-held scanning device. Current methods still do not provide for the restoration of the original contour of the teeth, anatomy, or occlusion (bite).

Current methods also require use of a milling device. These milling machines often utilize a diamond coated wheel to shape a block of ceramic or other tough material into the proper form for restoration.

Unfortunately, none of the current machines approaches the accuracy necessary to produce quality restorations. Current computer-assisted machine systems for dentistry rely on intra-oral photographic impressions from a hand-held scanner. These systems have failed to produce dental restorations of sufficient accuracy of fit for the dental profession. One area of notable disappointment has been the currently-utilized systems' inability to reproduce the appropriate contour and occlusion. Nor do the currently utilized systems assist in the design of the preparation of the dental prosthesis/restoration.

U.S. Pat. No. 3,861,044 describes a process in which a prepared tooth is scanned after inlay preparation. The prepared tooth is scanned to record proper side and bottom wall dimensions. Wax is then placed into the preparation and another scan is made. The two scans are then transferred to an automatic controlled machine tool. The above technique involves use of a relatively inaccurate hand-held scanning device and the placement of wax (a contaminant of the bonding procedure necessary to lute the dental restoration into place making this technique unusable in any practical sense). The wax requires carving intra-orally and is extremely reminiscent of the direct technique of inlay fabrication. Historically, this technique has been considered difficult.

U.S. Pat. No. 4,411,626 also utilizes modeling wax in its process. This patent describes using a model of the prepared "tooth stump" that is immobilized in a clamp and is scanned with a mechanical scanning head attached to a numerically-controlled processing machine. Modeling wax is applied to the stump and the wax milled to a uniform, computer-determined thickness and contour. The wax is then used for the casting of the dental restoration/prosthesis.

U.S. Pat. No. 5,092,022 describes a process of micro-sensing or direct optical impression for dental restorations/prosthesis construction utilizing computer assisted milling. This patent includes many methods of fabricating crowns, including the insertion of porcelain or plastic facings onto a fabricated metal framework.

Thus, a need arises for a method and apparatus for accurately and economically forming dental restorations/prostheses that will help eliminate costly laboratory involvement and the consequent necessity for return visits by the patient.

SUMMARY OF THE INVENTION

These needs and others are satisfied by the method and apparatus of the present invention for fabrication of a restoration for a patient's dentition by pinhead molding. The method comprises the steps of examining the patient's dentition, restoring gross areas of tooth loss, and restoring proper anatomy and contour of the dentition, forming a first optically correct impression of the dentition and scanning the first impression to provide a first data set, appropriately isolating and preparing the patient's dentition for the dental restoration, forming a second optically correct impression of the dentition and scanning the second impression to form a second data set, comparing the first and second data sets and deriving a third data based upon the comparison, the third data set being descriptive of a restoration to be prepared, and forming the restoration by pinhead molding of a flowable composite material in accordance with the third data set.

An apparatus is also described for fabrication of a restoration for a patient's dentition. The apparatus comprises means for scanning a first optically correct impression of the dentition after restoration of gross areas of tooth loss and restoration of proper anatomy and contour of the dentition to provide a first data set, means for scanning a second optically correct impression of the dentition after appropriate isolation and preparation of the patient's dentition to provide a second data set, means for comparing the first and second data sets to provide a third data set descriptive of a restoration to be prepared, and means for forming the restoration by pinhead molding of a flowable composite material in accordance with the third data set.

Further objects, features, and advantages of the present invention will become apparent from the following description and drawings.

DETAILED DESCRIPTION OF THE INVENTION

In accordance with the present invention, a method and apparatus for fabrication of dental restoration by pinhead molding are described that provide distinct advantages when compared to the prior art. Specifically, the described method and apparatus correct many of the real deficiencies found in previous methods and materials used for obtaining computer-assisted milled dental restorations/prostheses. The invention can best be understood with reference to the accompanying drawing figures.

Figure 1:
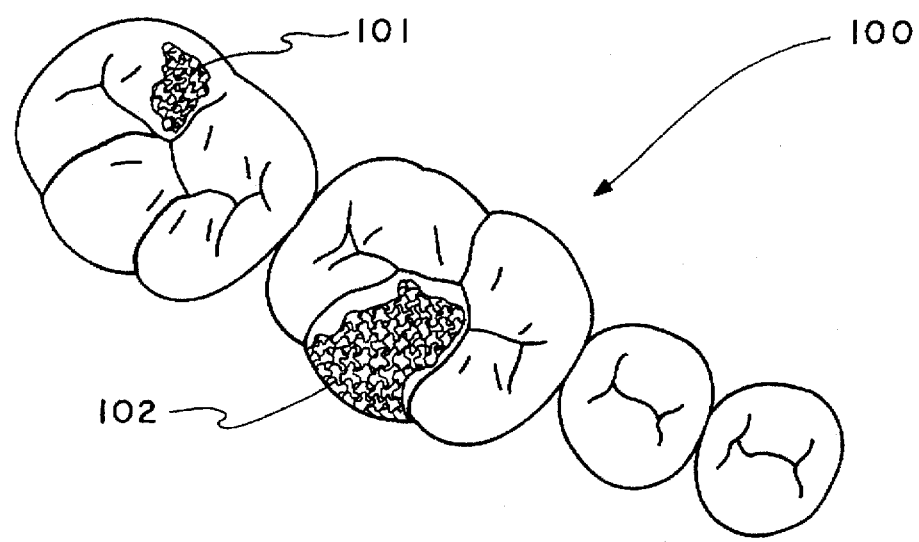
FIG. 1 is a view of the patient's dentition prior to establishment of normal occlusion, anatomy, and contours.

FIG. 1 illustrates a portion of the patient's dentition, generally depicted by the numeral 100, prior to establishment of normal occlusion, anatomy, and contours. The dentition 100 shows evidence of deep dental caries 101, 102 causing weakening of the tooth structure. In fact, there is considerable damage to the wall of the tooth at one of the sites 102, extensive enough to require an inlay for effective restoration of the dentition 100.

Figure 2:
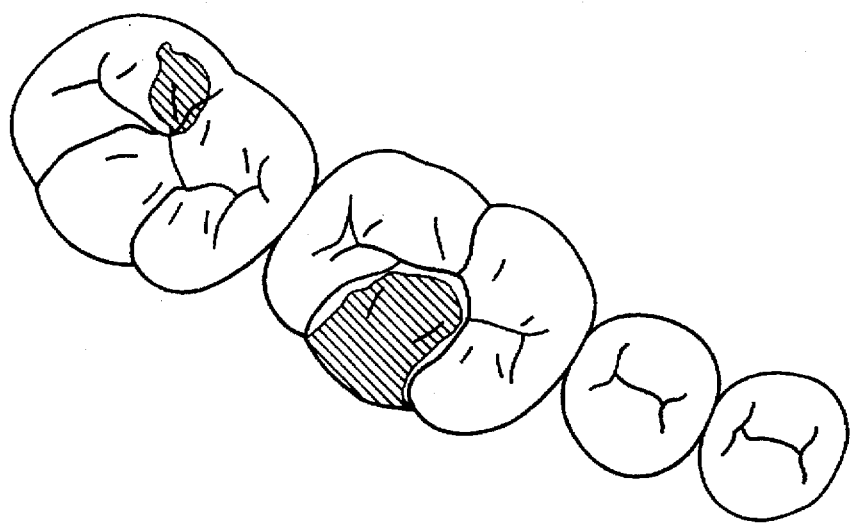
FIG. 2 is an illustration of the corrected dentition.

After examining the dentition 100, the practitioner generally adjusts any occlusal disharmonies, temporizes areas of gross caries, and restores the proper anatomy of the dentition. The corrected dentition is illustrated in FIG. 2.

Figure 3:
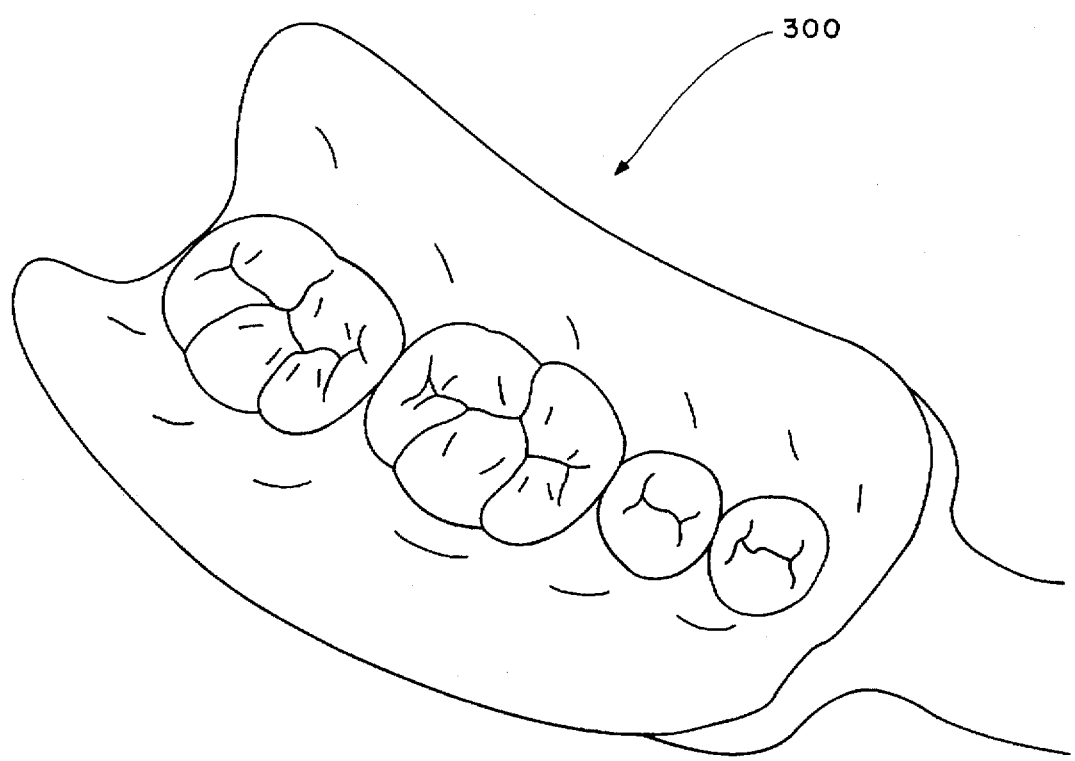
FIG. 3 is a representation of an optically correct impression of the dentition prior to preparation.

Next, an optically correct impression of the dentition is obtained prior to the preparation or shaping necessary for the restoration or prosthesis. Such an impression is illustrated in FIG. 3, generally depicted by the numeral 300. The impression material itself is color and optically neutral to enhance accuracy of a subsequent scanning operation.

The impression material may be either a polyether or addition reaction polyvinylsiloxane substance. These materials form very accurate impressions and are quite stable. Both materials are used extensively in dentistry and are readily adapted for use in the impression technique described herein. The materials are made optically neutral by reducing their reflectivity through the addition of black pigment.

An additional type of silicone impression material may be made by producing the base material through combination of a moderately low molecular weight silicone called a dimethyl siloxane, which has reactive terminal silane groups, with a filler of silicon that has been etched and treated (dyed or pigmented) to reduce reflectivity.

The accelerator is a moderately low molecular weight polymer with vinyl groups plus the treated filler and chloroplatinic acid catalyst. Palladium or platinum may be added to absorb any hydrogen gas produced. In addition, a surfactant may be added to improve the wettability.

Figure 4:
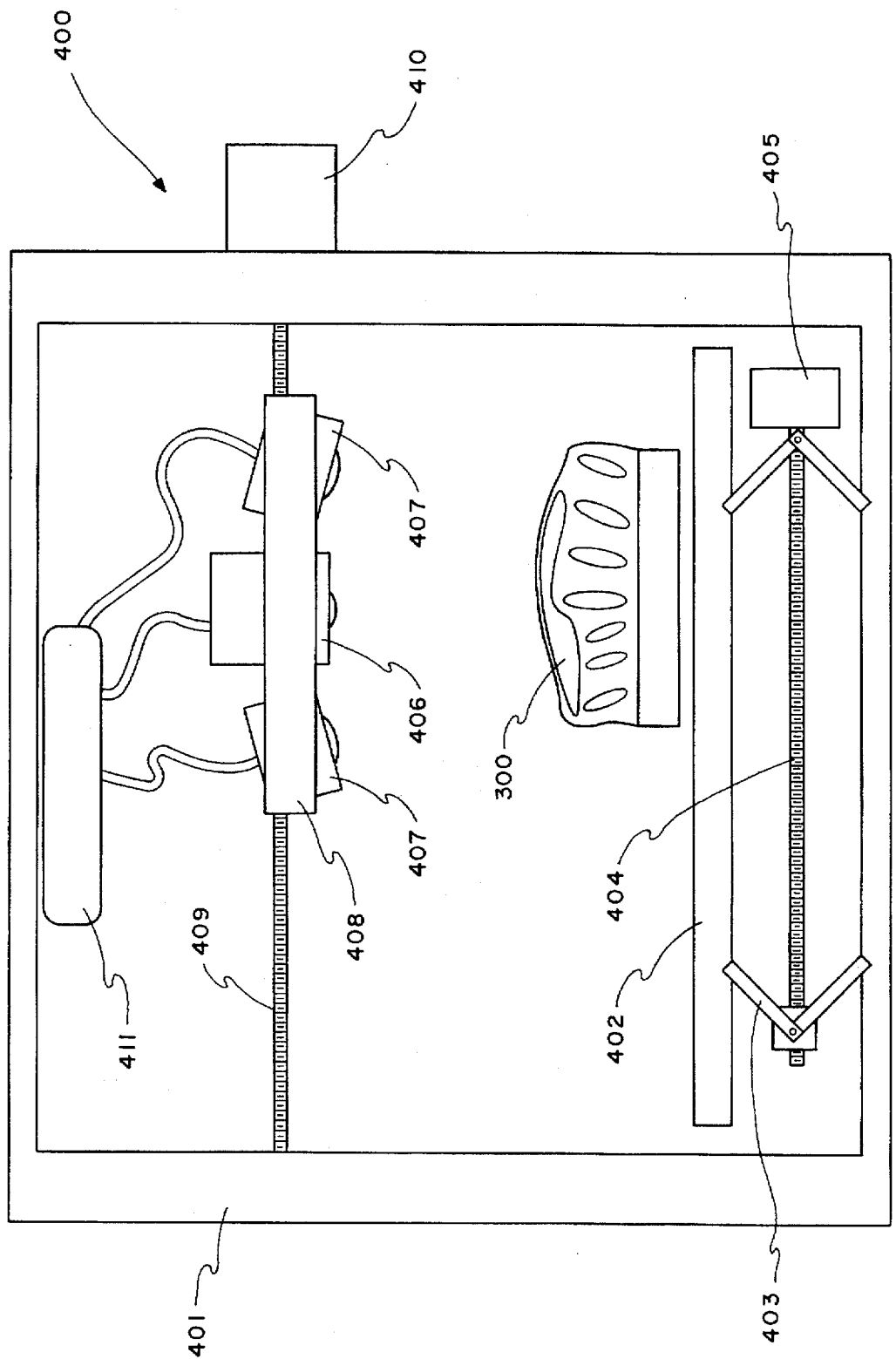
FIG. 4 is a representation of the optically neutral impression scanner.

This optically correct impression 300 is then placed in a stationary and centrally located laser scanning box, as shown in FIG. 4 and generally depicted by the numeral 400. Laser scanning is conducted within a controlled environment provided by enclosure 401, allowing for increased accuracy of the scanning and, consequently, of the produced restoration/prosthesis. There are no incidental stray light reflections due to the nonreflecting and optically neutral impression materials. The light sealed sensor enclosure 401 minimizes outside light source contamination.

The scanning device 400 itself is unique in that it utilizes an adjustable platform 402 which enables the scanning beam to create serial "slices" of the impression 300. The platform 402 is adjustable in a vertical direction by virtue of vertical adjustment mechanisms 403 actuated by an associated jackscrew 404 that is driven by a motor 405. The scanning beam from scanning laser source 406 sweeps continuously in a horizontal direction corresponding to movement into and out of the page in the view shown in FIG. 4.

The sliding laser source 406 scans each slice and the resulting reflected beams are recorded by light sensors 407 (cameras). The laser source 406 and sensors 407 are mounted to a circuit assembly 408 that is movable horizontally along another jackscrew 409 actuated by a motor 410. A power supply/control unit 411 supplies operating power to the laser 406 and sensors 407.

Once a complete scan of a particular impression 300 has been completed, the elevation of the platform 402 may be adjusted slightly, on the order of 1 millimeter, for example, and the scan repeated. Adjusting the height of the object 300 being scanned changes the parallax, or observation angle, for any undercut or otherwise obstructed features of the impression 300.

As the angle at which the beam from the laser source 406 impinges on a particular feature changes, new surface data is acquired that can help define surface features that may not be adequately mapped with the platform 402 at a fixed, constant elevation. Consequently, it may be helpful to adjust the platform 402 elevation multiple times and rescan the impression 300 in an iterative fashion to acquire multiple data sets for the same impression 300, which can then be analyzed and compared to more accurately identify potentially obstructed surface features of the impression. This iterative scan technique can lead to much greater accuracy in restoration formation.

Many types of laser scanners with associated sensors are known in the art. The scanning systems capture the surface geometry of the object being scanned and allow storage and transfer of the data representing object coordinates in a variety of formats. The set of data points measured and stored is a complete surface description of the object being scanned, and many available scanning units have scan resolutions on the order of 50 microns (20 points per millimeter) to provide a highly accurate representation of the scanned object.

After the first impression of the dentition (taken prior to preparation) has been scanned and the data stored to form a first set of impression data, the dentition is appropriately isolated and prepared for either a dental restoration or prosthesis. A second impression is then made of the dentition using the same optically neutral impression materials described above.

This second impression is also scanned to form a second set of impression data. Landmarks are established during both scans to facilitate subsequent data comparison. The available data sets are then imported into a CAD/CAM (computer-aided design/computer-aided manufacturing) program that drives a computer assisted molding machine in a manner to be described below.

Figure 5:
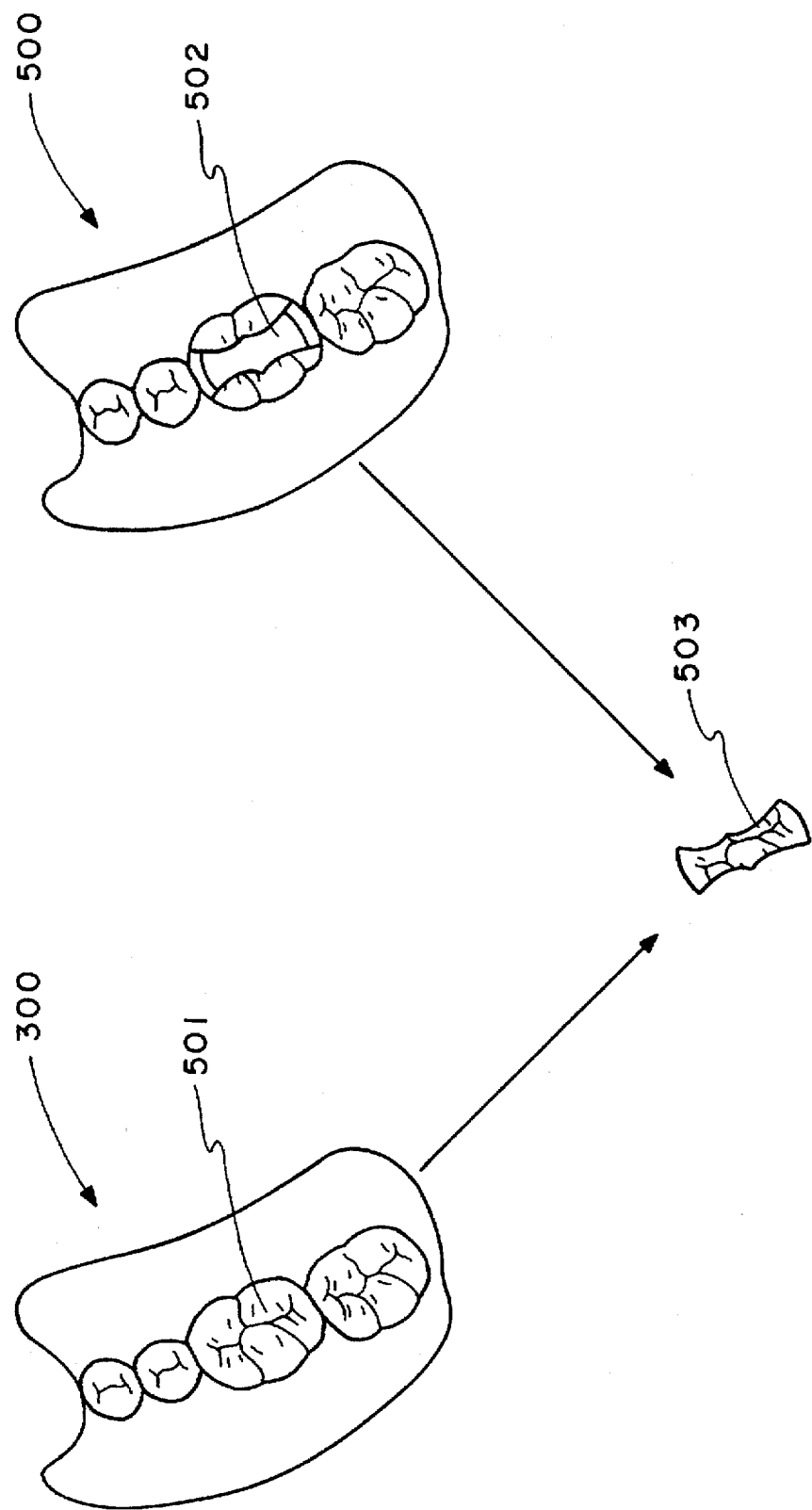
FIG. 5 illustrates how comparison of the data sets from the pre-preparation and post-preparation impressions yields the dimensions of the restoration.

FIG. 5 shows the fashion in which the laser scanner data set from the second impression 500 is subtracted from the data set obtained by scanning the first impression 300 to obtain the exact dimensions of the restoration 503. Note that the proper anatomy of the region 501 was restored prior to the first impression, while the region 502 of the dentition has been isolated and prepared for restoration or prosthesis prior to the second impression 500. Consequently, the dimensional data obtained from the two laser scanning operations are effectively compared or subtracted from one another to yield the proper dimensions for the restoration 503 itself.

Figure 7:
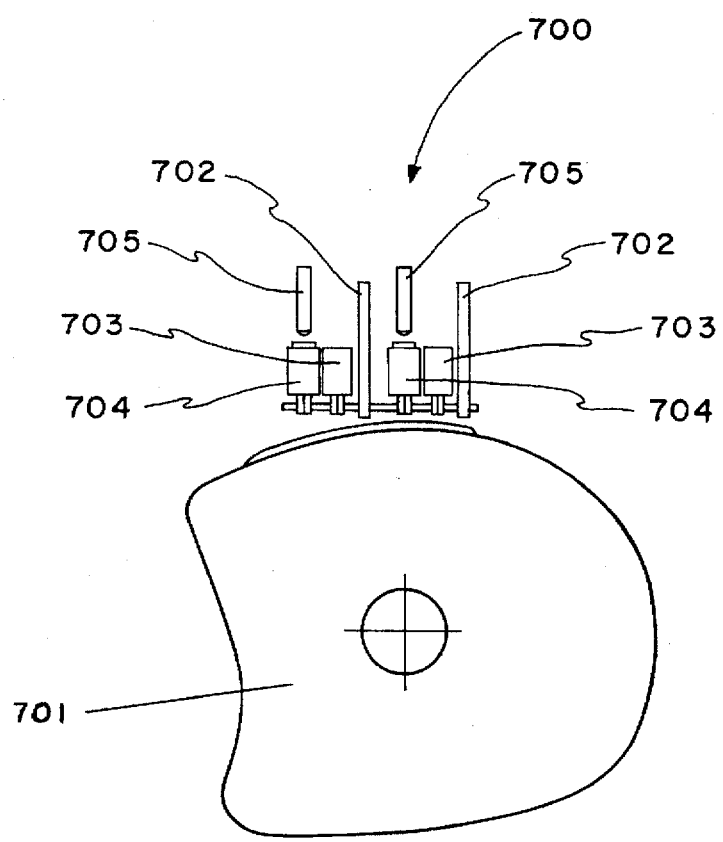
FIG. 7 is a diagram of the pinhead molding device in operation.
Figure 8A:
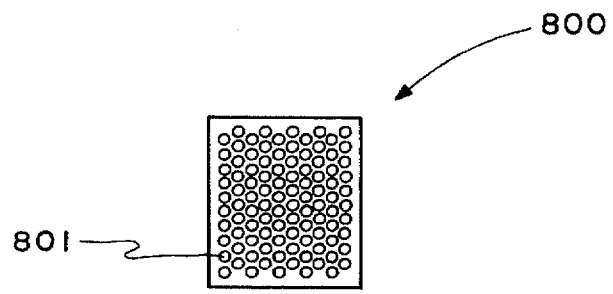
FIG. 8A depicts the pinhead molding array.

The computer assisted molding machine, generally depicted by the numeral 700 in FIG. 7, utilizes optically clear pinheads that have a coating of ferromagnetic material that allows the pinheads to move under the influence of a magnetic field in much the same way in which the pins of an impact print head move. Such printer pinhead assemblies are common in impact printers of the dot-matrix variety. An exemplary matrix 800 of pinheads 801 such as those used in the pinhead molding device 700 of the present invention is illustrated in FIG. 8A. FIG. 8A depicts a pinhead array 800 in a 10×10 matrix for the sake of simplicity of illustration. The actual pinhead array 800 is preferably a 50×50 matrix, although other arrangements may also be employed.

There are both initial forming pinheads 703 and detail pinheads 704 that form and then hold the flowable resin against an insert 701 for laser curing. The initial forming pinheads 703 are positioned in proximity to flowable composite tubes 702 that direct the flowable composite material onto the insert 701. The insert 701 may be constructed of porcelain, glass, or composite that has been etched and silanated to provide for a bond between the insert's 701 substrate and the flowable composite resin being layered on it. In addition, the block insert 701 may be constructed out of a composite material that will chemically bond to the layered flowable composite material applied and cured to it. Beta glass inserts have already been used to reinforce composite materials and could be used with this technique.

If Beta Quartz inserts are used, they are substantially superior in physical properties over currently used materials. The Beta Quartz inserts have compressive strengths similar to amalgam and Dicor restorations. The inserts are harder than porcelain and do not wear, stain, or discolor. The inserts have a thermal expansion lower than that of tooth structure and do not absorb water. The Beta Quartz inserts are made up of lithium aluminosilicate glass with microcrystalline properties. They also contain silicon dioxide, aluminum oxide, lithium oxide, and modifiers. The mix is melted, homogenized, and formed into inserts which can then be heat treated. The inserts are organofunctional silane coated for improved bonding to the flowable composite bonding material.

The choice of insert would be up to the clinician and may well depend upon the clinician's choice as to what stresses the final restoration may have placed on it. The choice as to what insert to use may also depend on the esthetics desired and the economic issues involved.

Figure 8B:
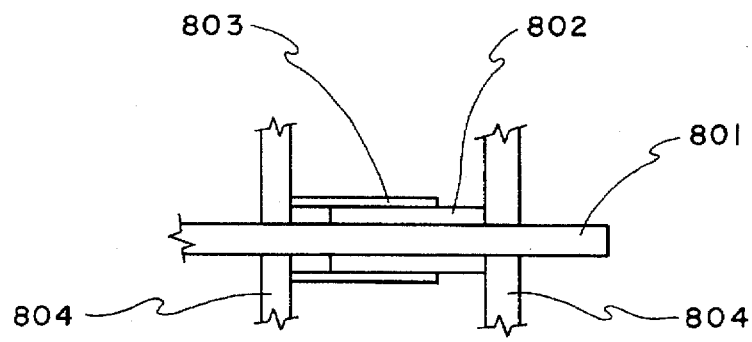
FIG. 8B is a detail view of a pin in the pinhead molding array.

This technique allows for very thin and minute layers of light curable "composite-like" materials to be accurately placed on the insert 701 to construct a well-fitting restoration. As shown in FIG. 8B, in order to place the flowable material accurately, the tips of each pinhead molding head 801 are quite small, formed of fiberoptic glass fibers of about 20 microns width. The ferromagnetic coating of the fiber 801 preferably begins about 20 microns from the end of the tip, allowing for movement of the pin 801 in both directions under the influence of the associated micro-wound coil 802 within sleeve 803. The pin assembly is supported within opposing plates 804.

Figure 8C:
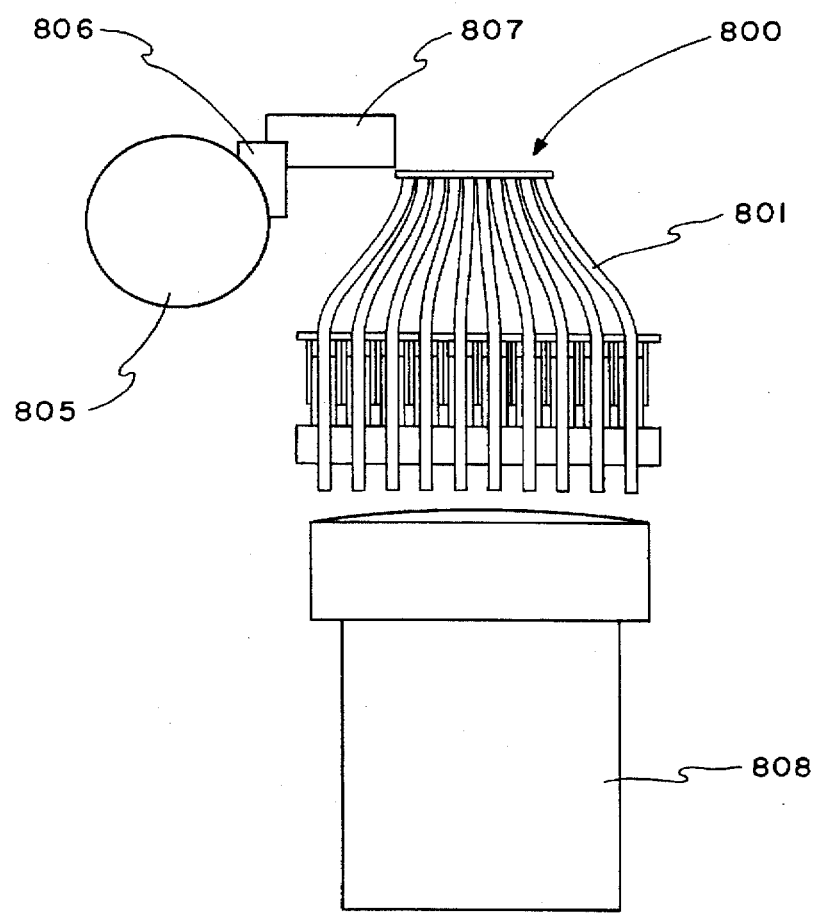
FIG. 8C is a side view of the pinhead molding array illustrating the composite reservoir and the curing laser.

FIG. 8C is a side view of the pinhead assembly illustrating a storage reservoir 805 for the flowable composite material that is preferably delivered through a composite material spreader 807 in advance of the pinhead assembly 800 by a pump 806. Since the pins 801 are formed from a flexible fiberoptic material, the pins 801 can be arranged in a spaced relationship through the actuating coils and then made to converge into the pinhead array 800, as shown. A laser irradiation source 808 is provided behind the pinhead assembly 800 so that the laser can be directed along the optical fiber pins 801 to cure the deposited composite material.

Figure 6:
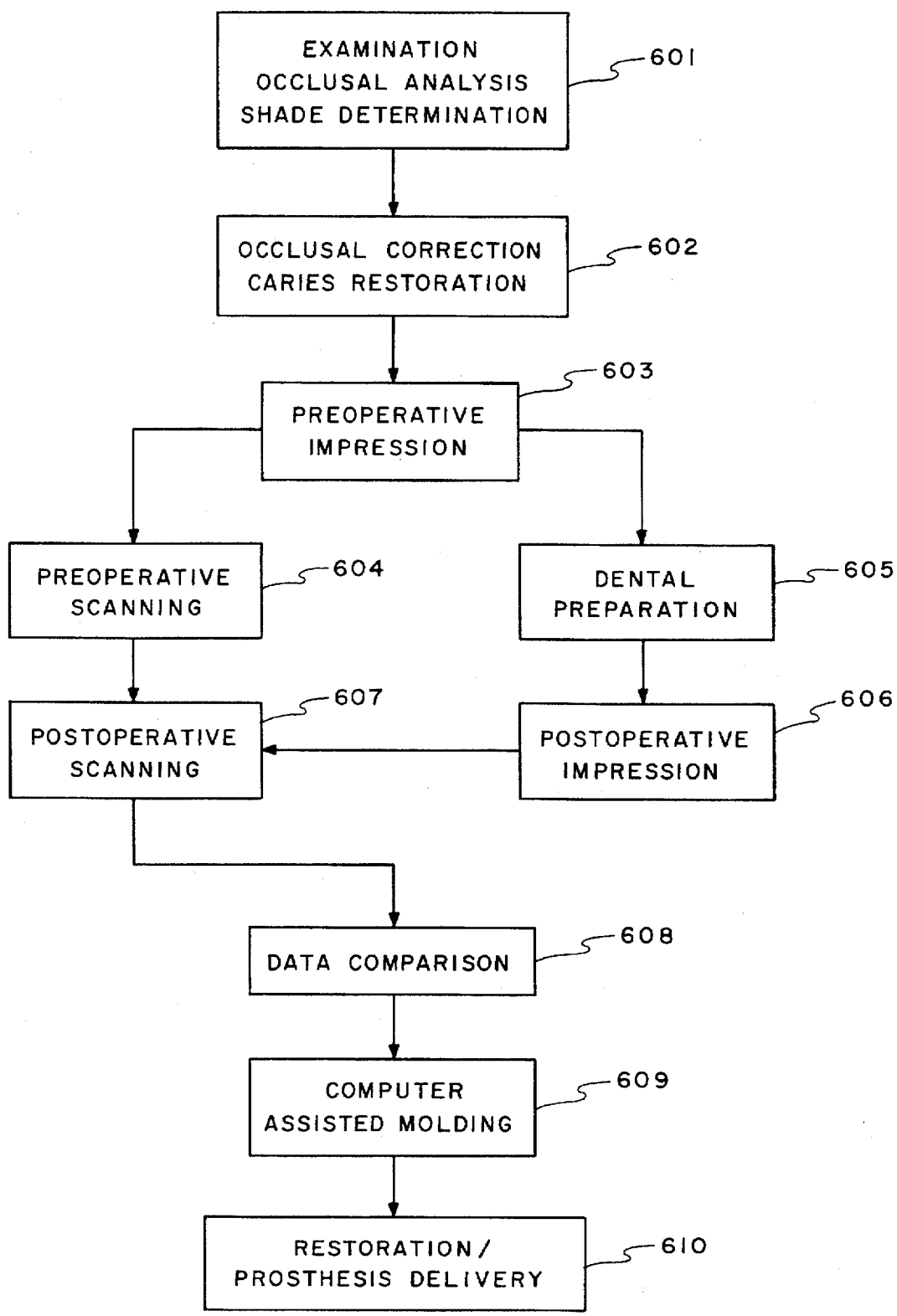
FIG. 6 is a flow chart of the method in accordance with the present invention.

FIG. 6 is a flow chart of the method in accordance with the present invention, generally depicted by the numeral 600. In the first step 601, the dentition is examined, subjected to occlusal analysis, and the proper shade of the restoration is determined. In the next operation 602, areas of gross caries are temporized, and proper anatomy of the dentition is restored. In the following operation 603, an optically correct impression is made, and is subjected to the pre-operative laser scanning operation in block 604.

The dentition is then appropriately isolated and prepared for either a restoration or prosthesis (step 605), and an optically correct post-operative impression is formed in the subsequent step 606. This post-operative impression is scanned in the laser scanner (step 607), and the two data sets provided by the scanning operations are imported to a CAD/CAM system for analysis and comparison in the subsequent step 608.

The comparison or substraction of the two data sets yields the proper dimension information for the computer assisted molding operation of step 609. The highly accurate pinhead molding process, followed by laser irradiation to cure the restoration, leads to rapid delivery of the restoration/prosthesis (step 610).

There have been described herein a method and apparatus for fabrication of dental restoration by pinhead molding that are relatively free from the shortcomings of the prior art. It will be apparent to those skilled in the art that modifications may be made without departing from the spirit and scope of the invention. Accordingly, it is not intended that the invention be limited except as may be necessary in view of the appended claims.

What is claimed is:

1. A method for fabrication of a restoration for a patient's dentition by pinhead molding, the method comprising the steps of:
   (a) examining the patient's dentition, restoring gross areas of tooth loss, and restoring proper anatomy and contour of the dentition;
   (b) forming a first optically correct impression of the dentition and scanning the first impression to provide a first data set;
   (c) appropriately isolating and preparing the patient's dentition for a dental restoration;
   (d) forming a second optically correct impression of the dentition and scanning the second impression to form a second data set;
   (e) comparing the first and second data sets and deriving a third data set based upon the comparison, the third data set being descriptive of a restoration to be prepared; and
   (f) forming the restoration by pinhead molding of a flowable composite material in accordance with the third data set.

2. The method in accordance with claim 1, wherein restoring gross areas of tooth loss comprises restoring gross areas of tooth loss with a temporary filling material.

3. The method in accordance with claim 1, wherein the steps of scanning the first and second impressions comprise scanning the first and second impressions in a laser scanner to provide first and second data sets of dimensional data for the first and second impressions.

4. The method in accordance with claim 3, wherein the laser scanner includes a vertically adjustable platform supporting the impression, and the step of scanning further comprises:
   (a) scanning the impression;
   (b) adjusting the vertically adjustable platform to vary platform height incrementally; and
   (c) repeating the scanning step.

5. The method in accordance with claim 1, wherein the step of comparing the first and second data sets comprises importing the first and second data sets to a CAD/CAM program that analyzes and subtracts the first and second data sets to form a third data set descriptive of a restoration to be formed.

6. The method in accordance with claim 1, wherein the step of forming the restoration comprises applying thin layers of flowable composite material to an insert in accordance with the third data set, in a pinhead molding process, to form a restoration of proper dimensions.

7. The method in accordance with claim 1, further including the step of curing the restoration.

8. A method for fabrication of a restoration for a patient's dentition by pinhead molding, the method comprising the steps of:
   (a) examining the patient's dentition;
   (b) adjusting the occlusion to optimize function of the dentition;
   (c) restoring gross areas of tooth loss with a temporary filling material;
   (d) preparing a first impression of the dentition to be restored;
   (e) scanning the first impression to provided a first set of impression data;
   (f) appropriately isolating and preparing the dentition;
   (g) preparing a second impression of the prepared dentition;
   (h) scanning the second impression to provide a second set of impression data;
   (i) comparing the first and second sets of impression data to generate a third set of data descriptive of the restoration to be prepared;
   (j) forming the restoration by pinhead molding of a flowable composite material in accordance with the third set of data; and
   (k) curing the composite material.

9. The method in accordance with claim 8, wherein the steps of scanning the first and second impressions comprise scanning the first and second impressions in a laser scanner to provide first and second data sets of dimensional data for the first and second impressions.

10. The method in accordance with claim 9, wherein the laser scanner includes a vertically adjustable platform supporting the impression, and the step of scanning further comprises:
    (a) scanning the impression;
    (b) adjusting the vertically adjustable platform to vary platform height incrementally; and
    (c) repeating the scanning step.

11. An apparatus for fabrication of a restoration for a patient's dentition comprising:
    means for scanning a first optically correct impression of the dentition after restoration of gross areas of tooth loss and restoration of proper anatomy and contour of the dentition to provide a first data set;
    means for scanning a second optically correct impression of the dentition after appropriate isolation and preparation of the patient's dentition to provide a second data set;
    means for comparing the first and second data sets and deriving a third data set based upon the comparison, the third data set being descriptive of a restoration to be prepared; and
    means for forming the restoration by pinhead molding of a flowable composite material in accordance with the third data set.

12. The apparatus of claim 11, wherein the means for scanning comprises a laser scanner.

13. The apparatus of claim 12, wherein the laser scanner comprises a laterally movable scanning laser, a plurality of optical sensors, and a vertically adjustable platform to accommodate an object to be scanned.

14. The apparatus of claim 13, wherein the laser scanner is housed in an enclosure that substantially prevents the entry of external illumination.

15. The apparatus of claim 11, wherein the means for comparing the first and second data sets comprises a CAD/CAM program.

16. The apparatus of claim 11, wherein the means for forming the restoration comprises a pinhead molding apparatus in which flowable composite material is deposited and shaped on an insert means.

17. The apparatus of claim 16, wherein the pinhead molding apparatus includes fiberoptic pins having a coating of ferromagnetic material such that the fiberoptic pins move in response to a magnetic field provided by an associated coil.

18. The apparatus of claim 17, further including a laser source directable onto the flowable composite material through the fiberoptic pins for curing the composite material.

* * * * *